(12) United States Patent
Wang et al.

(10) Patent No.: US 11,952,404 B2
(45) Date of Patent: Apr. 9, 2024

(54) TOMATO mSlBZR1L GENE AND USE THEREOF

(71) Applicant: ZHEJIANG UNIVERSITY, Zhejiang (CN)

(72) Inventors: Qiaomei Wang, Hangzhou (CN); Haoran Liu, Hangzhou (CN); Lihong Liu, Hangzhou (CN); Zhiyong Shao, Hangzhou (CN); Fanliang Meng, Hangzhou (CN); Dongyi Liang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 305 days.

(21) Appl. No.: 17/401,316

(22) Filed: Aug. 13, 2021

(65) Prior Publication Data

US 2022/0073573 A1  Mar. 10, 2022

Related U.S. Application Data

(63) Continuation of application No. PCT/CN2020/132274, filed on Nov. 27, 2020.

(30) Foreign Application Priority Data

Jan. 29, 2020  (CN) .......................... 202010080190.8

(51) Int. Cl.
  *C12N 15/82* (2006.01)
  *C07K 14/415* (2006.01)

(52) U.S. Cl.
  CPC ........ *C07K 14/415* (2013.01); *C12N 15/8262* (2013.01)

(58) Field of Classification Search
  None
  See application file for complete search history.

(56) References Cited

FOREIGN PATENT DOCUMENTS

| CN | 109628453 A | 4/2019 | |
|---|---|---|---|
| CN | 111088263 A | 5/2020 | |
| KR | 2017115774 A | * 10/2017 | ........... C07K 14/415 |
| WO | 2014203949 A1 | 12/2014 | |

OTHER PUBLICATIONS

International Search Report (PCT/CN2020/132274); dated Mar. 3, 2021.
"BZR1 Mediates Brassinosteroid-Induced Autophagy and Nitrogen Starvation in Tomato" (Feb. 28, 2019) [Yu Wang et al.].
"Genetic Transformation and Functional Analysis of SlBZR1Gene in Tomato" (Sep. 15, 2015) [Chen, Delong].
"Solanum lycopersicum protein Brassinazole-Resistant 1 (BZR1),mRNA" (Sep. 3, 2019) [Wang Y et al.].

* cited by examiner

*Primary Examiner* — Matthew R Keogh
(74) *Attorney, Agent, or Firm* — W&G Law Group

(57) ABSTRACT

The present disclosure relates to the field of biotechnology, and particularly to use of a tomato gene mSlBZR1L in changing the morphology of tomato fruits. The present disclosure discloses a tomato gene mSlBZR1L comprising a nucleotide sequence as set forth in SEQ ID No: 3, and the gene can extend the length of the tomato fruits.

4 Claims, 5 Drawing Sheets

Specification includes a Sequence Listing.

SEQ ID No: 1

ATGATGTGGGAAGGTGGAGGGTTGCCGGTGGAGGGTGGTGGTGGTGTTGGTGAAGGTG
GTGGTGTTGGTGGTGGTGGAGGTGGTGGTAGTGGGAGGAGGAAGCCATCATGGAGGGA
AAGGGAGAATAATAGGAGGAGGGAAAGGAGGAGAAGGGCAATAGCAGCTAAGATTTAT
AGTGGATTAAGAGCACAGGGGAATTATAATCTTCCTAAACATTGTGATAACAATGAGGTT
TTGAAGGCTCTTTGTGTTGAAGCTGGATGGATTGTTGAGCCTGATGGAACTACTTATAGA
AAGGGATGCAGGCCAACTCCAATGGAGATTGGAGGCACTTCAGCCAACATTACGCCAA
GTTCTTCACGAAATCCAAGTCCTCCCTCTTCATACTTTGCTAGCCCGATTCCATCTTACCA
AGTTAGTCCAACATCCTCGTCTTTCCCAAGTCCATCTCGTGGTGATGCTAACATGTCGTC
ACATCCATTTGCATTTCTCCATAGTTCCATTCCCTTGTCGCTACCACCATTACGAATATCAA
ACAGTGCCCCTGTAACACCACCTCTTTCATCACCAACTAGAGTCCCTAAGCAGATATTTA
ATCTTGAGACTTTGGCTAGAGAGTCTATGTCTGCTCTAAATATCCCTTTCTTTGCTGCTTC
AGCCCCAACTAGCCCAACTCGAGGTCAGCGATTCACTCTGCTACAATACCAGAGTGTG
ACGAATCTGATTCATCCACCATTGATTCTGGCCAGTGGATGAGCTTTCAAAAGTACGCAG
CCAATGGGATCCCTACTTCTCCGACTTTTAATCTTATTAAGCCTGTAGCTCAGAGAATTCC
TTCTAATGATATGATCATCGACAAGGGTAAGAGCATTGAATTTGACTTTGAGAATGTATCA
GTTAAGGCAGCATGGGAAGGTGAAAAGATTCATGAGGTTGGTTTAGATGATCTGGAGCT
CACTCTCGGAAGTGGGACTGCTCGGATG

SEQ ID No: 2

MMWEGGGLPVEGGGGVGEGGGVGGGGGGGSGRRKPSWRERENNRRRERRRRAIAAKIY
SGLRAQGNYNLPKHCDNNEVLKALCVEAGWIVEPDGTTYRKGCRPTPMEIGGTSANITPSS
SRNPSPPSSYFASPIPSYQVSPTSSSFPSPSRGDANMSSHPFAFLHSSIPLSLPPLRISNSAPVTPP
LSSPTRVPKQIFNLETLARESMSALNIPFFAASAPTSPTRGQRFTATIPECDESDSSTIDSGQW
MSFQKYAANGIPTSPTFNLIKPVAQRIPSNDMIIDKGKSIEFDFENVSVKAAWEGEKIHEVGL
DDLELTLGSGTARM

FIG. 5

SEQ ID No : 3

ATGATGTGGGAAGGTGGAGGGTTGCCGGTGGAGGGTGGTGGTGGTGTTGGTGAAGGTG
GTGGTGTTGGTGGTGGTGGAGGTGGTGGTAGTGGGAGGAGGAAGCCATCATGGAGGGA
AAGGGAGAATAATAGGAGGAGGGAAAGGAGGAGAAGGGCAATAGCAGCTAAGATTTAT
AGTGGATTAAGAGCACAGGGGAATTATAATCTTCCTAAACATTGTGATAACAATGAGGTT
TTGAAGGCTCTTTGTGTTGAAGCTGGATGGATTGTTGAGCCTGATGGAACTACTTATAGA
AAGGGATGCAGGCCAACTCCAATGGAGATTGGAGGCACTTCAGCCAACATTACGCCAA
GTTCTTCACGAAATCCAAGTCCTCCCTCTTCATACTTTGCTAGCCCGATTCCATCTTACCA
AGTTAGTCCAACATCCTCGTCTTTCCCAAGTCCATCTCGTGGTGATGCTAACATGTCGTC
ACATCCATTTGCATTTCTCCATAGTTCCATTCCCTTGTCGCTACCACCATTACGAATATCAA
ACAGTGCCCCTGTAACACCACCTCTTTCATCACCAACTAGAGTCCCTAAGCAGATATTTA
ATCTTGAGACTTTGGCTAGAGAGTCTATGTCTGCTCTAAATATCCCTTTCTTTGCTGCTTC
AGCCCCAACTAGCCCAACTCGAGGTCAGCGATTCACTCTTGCTACAATACCAGAGTGTG
ACGAATCTGATTCATCCACCATTGATTCTGGCCAGTGGATGAGCTTTCAAAAGTACGCAG
CCAATGGGATCCCTACTTCTCCGACTTTTAATCTTATTAAGCCTGTAGCTCAGAGAATTCC
TTCTAATGATATGATCATCGACAAGGGTAAGAGCATTGAATTTGACTTTGAGAATGTATCA
GTTAAGGCAGCATGGGAAGGTGAAAAGATTCATGAGGTTGGTTTAGATGATCTGGAGCT
CACTCTCGGAAGTGGGACTGCTCGGATG

SEQ ID No : 4

MMWEGGGLPVEGGGGVGEGGGVGGGGGGGSGRRKPSWRERENNRRRERRRRAIAAKIY
SGLRAQGNYNLPKHCDNNEVLKALCVEAGWIVEPDGTTYRKGCRPTPMEIGGTSANITPSS
SRNPSPPSSYFASPIPSYQVSPTSSSFPSPSRGDANMSSHPFAFLHSSIPLSLPPLRISNSAPVTPP
LSSPTRVPKQIFNLETLARESMSALNIPFFAASAPTSPTRGQRFTLATIPECDESDSSTIDSGQW
MSFQKYAANGIPTSPTFNLIKPVAQRIPSNDMIIDKGKSIEFDFENVSVKAAWEGEKIHEVGL
DDLELTLGSGTARM

FIG. 6

TOMATO mSlBZR1L GENE AND USE THEREOF

TECHNICAL FIELD

The present disclosure relates to the field of biotechnology, and particularly to use of a tomato mSlBZR1L gene in changing the morphology of tomato fruits.

BACKGROUND

Tomato is native to South America and is one of the most widely cultivated vegetables in the world. Planting area and output of tomato in China are among the top in the world. At the same time, tomatoes are also an important model plant in the field of fruit science research due to easy genetic transformations and various mutants of fruit characters.

The morphology of tomato fruits, as an important part of the sensory quality of tomato fruit, has always been concerned by consumers and scientific researchers. The morphology of tomato fruit includes shape and volume of the fruit. Specifically, the shape of the fruits is mainly described quantitatively by shape index. For example, an increase in the shape index indicates that the fruit is elongated vertically, and a decrease in the shape index indicates that the fruit grows horizontally. In previous studies, forward genetics is used to locate genes that cause changed in the morphology of the fruit, and then genetic transformation is used to prove the effect of the genes on the morphology and structure of the tomato fruits.

SUMMARY

A technical problem to be solved by the present disclosure is to provide a mSlBZR1L gene and use thereof.

In order to solve the technical problem above, the present disclosure provides a tomato mSlBZR1L gene (a gene mSlBZR1L that regulates the morphology of tomato fruits), wherein the nucleotide sequence of the gene mSlBZR1L is as shown in SEQ ID NO: 3.

The present disclosure also provides a protein encoded by the gene mSlBZR1L, wherein the amino acid sequence of the protein is as shown in SEQ ID NO: 4.

The present disclosure also provides use of the gene mSlBZR1L in changing the morphology of tomato fruits; specifically, the gene mSlBZR1L is used in extending the length of the tomato fruits.

That is, the present disclosure also provides use of the gene mSlBZR1L in constructing a transgenic tomato, wherein the transgenic tomato has changed shape, and said changed shape can be an elongated fruit shape.

In the present disclosure, base C at position 695 of the nucleotide sequence of the tomato homologous gene SlBZR1L of the core transcription factor BES1 involving the signal transduction pathway of brassinolide (BR) is mutated to T, so that the corresponding amino acid residue P at position 232 of the amino acid sequence of SlBZR1L is mutated to L, resulting in a new gene mSlBZR1L. The over-expression of the new gene mSlBZR1L in the tomato fruit leads to an elongated fruit. Most studies on the BES1 were previously focused on the resistance to adversity of *Arabidopsis* having said gene, while its function on the morphology of the tomato fruit has not been reported.

The present disclosure constructed a plant overexpressing tomato mSlBZR1L gene for the first time, and conducted functional research on it. It was found that the mSlBZR1L gene plays a positive role in the regulation of the morphological elongation of the tomato fruit through measuring the morphology of the fruit.

BRIEF DESCRIPTION OF DRAWINGS

In order to make the objectives, technical solutions, and advantages of the present disclosure clearer, the specific embodiments of the present disclosure will be further described in detail in combination with the accompanying drawings below.

FIG. 5 shows the nucleotide sequence of the gene SlBZR1L and the amino acid sequence of the protein encoded by the nucleotide sequence;

FIG. 6 shows the nucleotide sequence of the gene mSlBZR1L and the amino acid sequence of the protein encoded by the nucleotide sequence.

DESCRIPTION OF EMBODIMENTS

Figure 1:
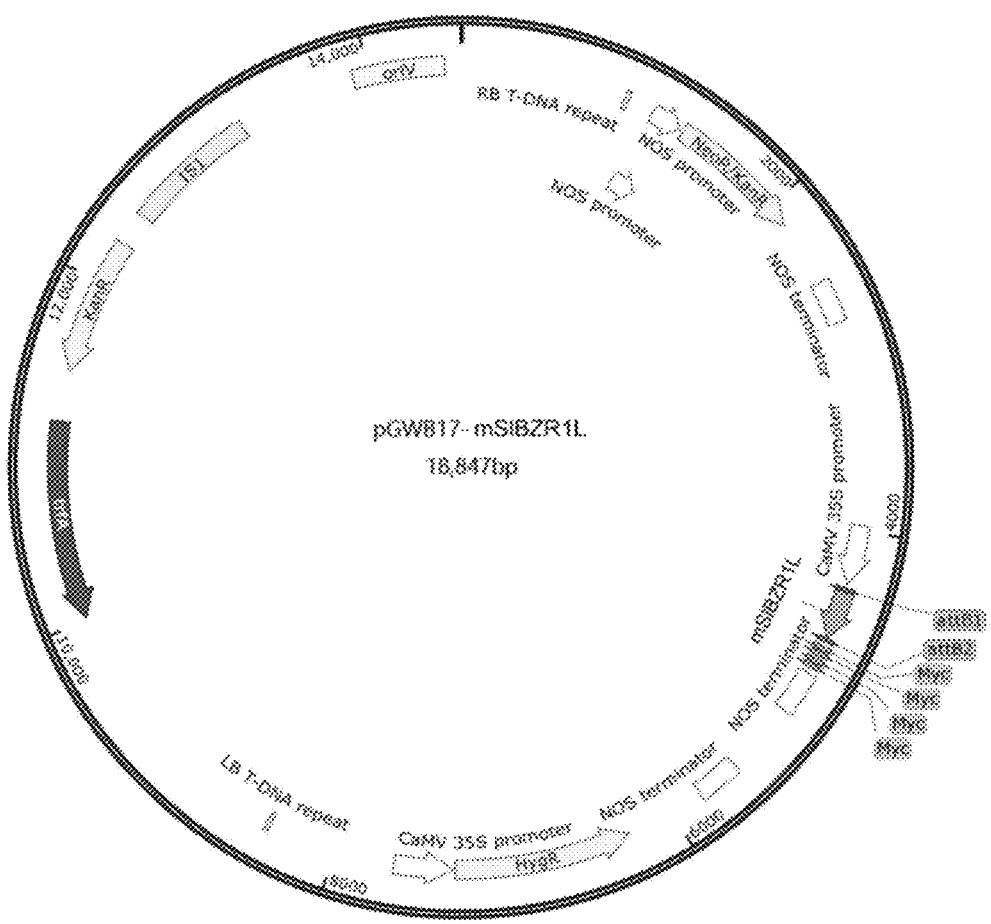
FIG. 1 shows a vector profile of the mSlBZR1L gene—overexpressing vector pGWB17::mSlBZR1L.

The present disclosure will be further described in combination with specific embodiments below, but the protection scope of the present disclosure is not limited thereto:

1. Acquiring of the Full-Length Sequence of the Tomato SlBZR1L Gene:

Primers used in whole genome amplification were designed using Primer Premier 6.0. cDNA extracted from leaves of a wild-type tomato Craigella grown in the greenhouse of Zijingang Campus of Zhejiang University was taken as a template (the cDNA can be extracted by a conventional technology, for example, that disclosed in CN 104561025 A) for the design of specific primers SlBZR1L-F and SlBZR1L-R, and the SlBZR1L fragment was amplified by PCR using PrimerSTAR high-fidelity enzyme.

Sequences of the primers:

SlBZR1L-F: 5'-ATGTGGGAAGGTGGAGGGTTGC-3'

SlBZR1L-R: 5'-CATCCGAGCAGTCCCACTTCCGA-3'

Reaction system for PCR amplification: 2× PrimerSTAR buffer 25 ul, dNTP Mixture 5 ul, PrimerSTAR DNA polymerase 1 ul, ddH$_2$O 16 ul, cDNA1 ul, and upstream primers 1 ul and downstream primers 1 ul, 50 ul in total. The PCR procedure includes: performing pre-denaturation at 94° C. for 90 seconds; denaturation at 94° C. for 30 seconds, annealing at 57° C. for 45 seconds, extending at 72° C. for 1 minute, 35 cycles; final extending at 72° C. for 5 minutes; the obtained PCR product was identified by electrophoresis using 1% agarose gel, and then the amplified band was recovered and purified using Axygen DNA gel kit, and the recovered product was constructed into the pQB-V3 vector, and the obtained recombinant plasmid pQB-V3-SlBZR1L was delivered to TSINGKE corporation for sequencing and confirmation.

The nucleotide sequence of the resulting gene SlBZR1L is as shown in SEQ ID No: 1; the amino acid sequence of the protein encoded by the gene is as shown in SEQ ID No: 2. As shown in FIG. 5, where the underline mark indicates a single base or a single amino acid to be changed.

2. Acquiring of the Full-Length Gene Sequence of the Modified Gene mSlBZR1L

Primers used in whole genome amplification were designed using Primer Premier 6.0, the plasmid pQB-V3-SlBZR1L constructed above was taken as a template to design specific primers mSlBZR1L-F and mSlBZR1L-R, and by combining the above-mentioned primers SlBZR1L-F and SlBZR1L-R, two segments of PCR products were obtained by amplifying using the combination of SlBZR1L-F and mSlBZR1L-R and the combination of mSlBZR1L-F and SlBZR1L-R respectively (see section 1 above for the reaction system for PCR amplification), and the overlapping part of the two segments covers the mutation position of the single base. The above amplification was performed by PCR using PrimerSTAR high-fidelity enzyme. Then, the full length of mBZR1L was amplified using these two segments of PCR products as templates and the SlBZR1L-F and SlBZR1L-R as primers.

Sequences of the primers:
mSlBZR1L-F: 5'-ATTCACTCTTGCTACAATAC-3'
mSlBZR1L-R: 5'-GTATTGTAGCAAGAGTGAAT-3'

The nucleotide sequence of the resulting gene mSlBZR1L is as shown in SEQ ID No: 3, where the underline mark indicates a different nucleotide from that of SlBZR1L; the amino acid sequence of the protein encoded by the gene is as shown in SEQ ID No: 4. As shown in FIG. 6, where the underline mark indicates a different amino acid from that of SlBZR1L.

3. Construction of mSlBZR1L Gene Overexpressing Vector

The construction of mSlBZR1L overexpressing vector was conducted by using pGWB17 as the final vector, and constructing the pGWB17-35S::mSlBZR1L vector having the CaMV35S recombinant overexpression promoter. Specifically, the construction was as follows:

The target fragment (SEQ ID No: 3) was transferred from the original pQB-V3 vector (i.e., the pQB-V3-mSlBZR1L obtained from the acquiring of the full-length gene sequence of the modified gene mSlBZR1L in section 2 above) to the final vector pGWB17 to give a pGWB17-mSlBZR1L plasmid. Gateway® LR Clonase® II Enzyme mix (Thermo Fisher) kit was used following the instructions in the kit.

The pGWB17-35S::mSlBZR1L plasmid was transferred into Top10 competent *E. coli*. Screening was conducted by the coating method, and colony PCR was used to screen out the pGWB17 recombinant plasmid carrying the target fragment (the pGWB17 recombinant plasmid was one that having a band size of about 1000 bp). sequencing and identification were then conducted. DNAMAN software was used to analyze the sequencing results. The correct transformant was named pGWB17::mSlBZR1L (FIG. 1).

4. Construction and Detection of Transgenic Materials:

Conjugative transfer of the overexpression vector pGWB17::mSlBZR1L to *Agrobacterium* LBA4404 was conducted, and the *Agrobacterium* LBA4404 was then used to infect the tomato cotyledons. Tissue culture plantlets were obtained through callus induction, resistance induced differentiation and rooting culture. The positive transgenic plants were verified by PCR and RT-PCR. The T2 generation seeds were sown on a medium containing kanamycin (50 mg/L) to germinate, and 5 overexpression transgenic lines were obtained.

Figure 2:
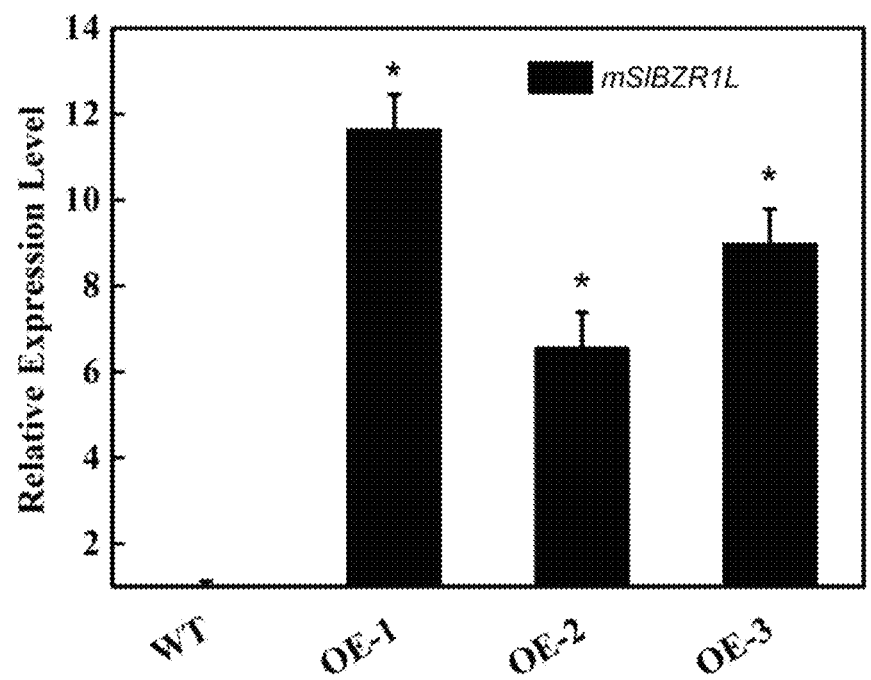
FIG. 2 shows an expression level of mSlBZR1L gene in mSlBZR1L gene overexpressing fruits.

Explanation: the separation ratio of seeds growing lateral roots to seed without growing lateral roots on the medium containing kanamycin (50 mg/L) meets 3:1 and the gene expression level is increased by two folds or more are defined as overexpression. Three overexpression plant lines with high gene transcription levels were selected as the research objects (FIG. 2).

Figure 3:
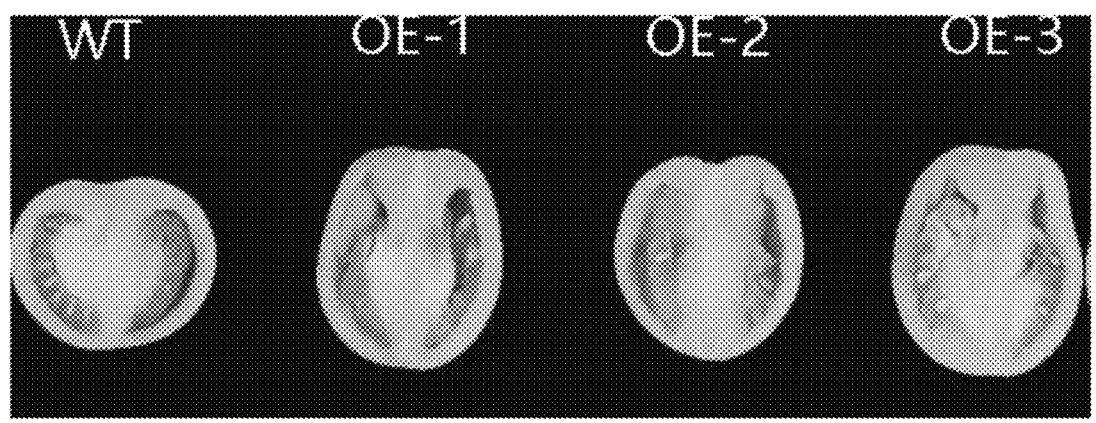
FIG. 3 shows morphological structures of the mSlBZR1L gene overexpressing fruits.

In FIG. 3, WT represents wild-type non-transgenic tomato Craigella, and OE-1, OE-2, and OE-3 respectively represent an overexpression line of mSlBZR1L.

5. Research on the Morphology of the Transgenic Tomato Fruit

The wild-type and transgenic materials were planted in the same greenhouse at the Huajiachi Vegetable Base of Zhejiang University. Fruits at mature-green stage (green fruits 35 days after flowering) without obvious mechanical damage were harvested from the same fruit position of the wild-type and transgenic materials. The fruits were cut vertically and taken pictures (FIG. 3). A vernier caliper was used to measure the vertical and horizontal diameters of the fruits, and the shape index was calculated (FIG. 4) from an equation: shape index=vertical diameter of the fruit/horizontal diameter of the fruit.

Figure 4:
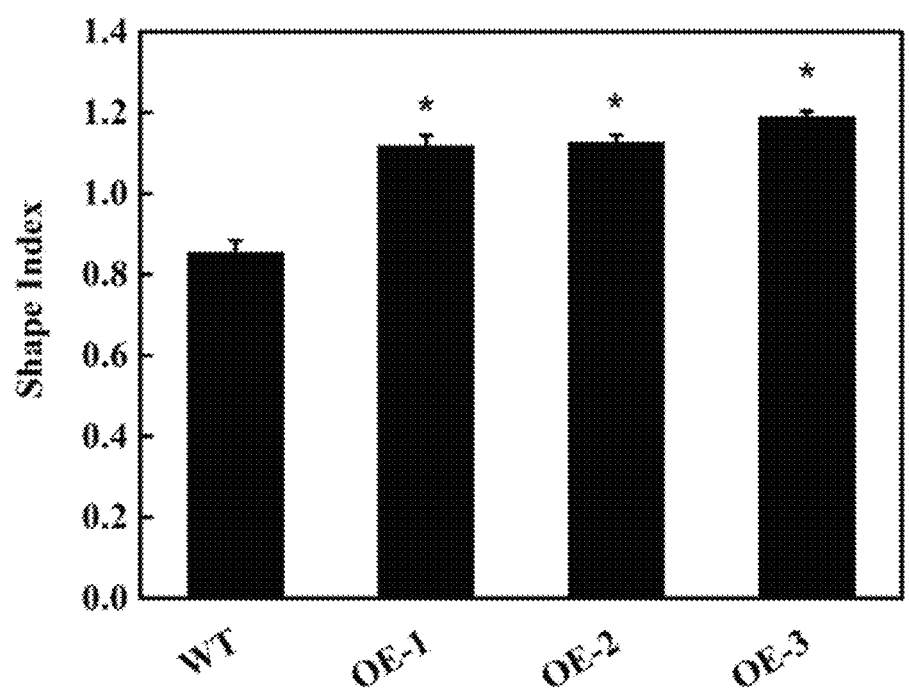
FIG. 4 shows a shape index of the mSlBZR1L gene overexpressing fruits.

According to FIG. 4, it can be seen that the modified tomato gene mSlBZR1L can change the morphology of the tomato fruit and extend the fruit length.

Finally, it should also be noted that the above-listed are only a few specific embodiments of the present disclosure. Obviously, the present invention is not limited to the above embodiments, and many variations are possible. All the variations that can be directly derived or suggested by those skilled in the art from the present disclosure should be considered as within the scope of the invention.

SEQUENCE LISTING

```
<160> NUMBER OF SEQ ID NOS: 4

<210> SEQ ID NO 1
<211> LENGTH: 984
<212> TYPE: DNA
<213> ORGANISM: Artificial Sequence
<220> FEATURE:
<223> OTHER INFORMATION: the tomato homologous gene of the core
      transcription factor BES1 involving the signal transduction
      pathway of brassinolide (BR)

<400> SEQUENCE: 1
atgatgtggg aaggtggagg gttgccggtg gagggtggtg gtggtgttgg tgaaggtggt      60
ggtgttggtg gtgtggagg tggtggtagt gggaggagga agccatcatg gagggaaagg     120
gagaataata ggaggaggga aaggaggaga agggcaatag cagctaagat ttatagtgga     180
```

```
ttaagagcac aggggaatta taatcttcct aaacattgtg ataacaatga ggttttgaag    240
gctctttgtg ttgaagctgg atggattgtt gagcctgatg aaactactta tagaaaggga    300
tgcaggccaa ctccaatgga gattggaggc acttcagcca acattacgcc aagttcttca    360
cgaaatccaa gtcctccctc ttcatacttt gctagcccga ttccatctta ccaagttagt    420
ccaacatcct cgtctttccc aagtccatct cgtggtgatg ctaacatgtc gtcacatcca    480
tttgcatttc tccatagttc cattcccttg tcgctaccac cattacgaat atcaaacagt    540
gcccctgtaa caccacctct ttcatcacca actagagtcc ctaagcagat atttaatctt    600
gagactttgg ctagagagtc tatgtctgct ctaaatatcc ctttctttgc tgcttcagcc    660
ccaactagcc caactcgagg tcagcgattc actcctgcta caataccaga gtgtgacgaa    720
tctgattcat ccaccattga ttctggccag tggatgagct ttcaaaagta cgcagccaat    780
gggatcccta cttctccgac ttttaatctt attaagcctg tagctcagag aattccttct    840
aatgatatga tcatcgacaa gggtaagagc attgaatttg actttgagaa tgtatcagtt    900
aaggcagcat gggaaggtga aaagattcat gaggttggtt tagatgatct ggagctcact    960
ctcggaagtg ggactgctcg gatg                                           984
```

```
<210> SEQ ID NO 2
<211> LENGTH: 328
<212> TYPE: PRT
<213> ORGANISM: Artificial Sequence
<220> FEATURE:
<223> OTHER INFORMATION: amino acid sequence encoded by S1BZR1L

<400> SEQUENCE: 2

Met Met Trp Glu Gly Gly Leu Pro Val Glu Gly Gly Gly Gly Gly Val
1               5                   10                  15

Gly Glu Gly Gly Gly Val Gly Gly Gly Gly Gly Gly Ser Gly Arg
            20                  25                  30

Arg Lys Pro Ser Trp Arg Glu Arg Asn Asn Arg Arg Glu Arg
        35                  40                  45

Arg Arg Arg Ala Ile Ala Ala Lys Ile Tyr Ser Gly Leu Arg Ala Gln
50                  55                  60

Gly Asn Tyr Asn Leu Pro Lys His Cys Asp Asn Asn Glu Val Leu Lys
65                  70                  75                  80

Ala Leu Cys Val Glu Ala Gly Trp Ile Val Glu Pro Asp Gly Thr Thr
                85                  90                  95

Tyr Arg Lys Gly Cys Arg Pro Thr Pro Met Glu Ile Gly Gly Thr Ser
            100                 105                 110

Ala Asn Ile Thr Pro Ser Ser Ser Arg Asn Pro Ser Pro Pro Ser Ser
        115                 120                 125

Tyr Phe Ala Ser Pro Ile Pro Ser Tyr Gln Val Ser Pro Thr Ser Ser
    130                 135                 140

Ser Phe Pro Ser Pro Ser Arg Gly Asp Ala Asn Met Ser Ser His Pro
145                 150                 155                 160

Phe Ala Phe Leu His Ser Ser Ile Pro Leu Ser Leu Pro Pro Leu Arg
                165                 170                 175

Ile Ser Asn Ser Ala Pro Val Thr Pro Leu Ser Ser Pro Thr Arg
            180                 185                 190

Val Pro Lys Gln Ile Phe Asn Leu Glu Thr Leu Ala Arg Glu Ser Met
        195                 200                 205

Ser Ala Leu Asn Ile Pro Phe Phe Ala Ala Ser Ala Pro Thr Ser Pro
```

Thr Arg Gly Gln Arg Phe Thr Pro Ala Thr Ile Pro Glu Cys Asp Glu
225                 230                 235                 240

Ser Asp Ser Ser Thr Ile Asp Ser Gly Gln Trp Met Ser Phe Gln Lys
            245                 250                 255

Tyr Ala Ala Asn Gly Ile Pro Thr Ser Pro Thr Phe Asn Leu Ile Lys
            260                 265                 270

Pro Val Ala Gln Arg Ile Pro Ser Asn Asp Met Ile Ile Asp Lys Gly
        275                 280                 285

Lys Ser Ile Glu Phe Asp Phe Glu Asn Val Ser Val Lys Ala Ala Trp
    290                 295                 300

Glu Gly Glu Lys Ile His Glu Val Gly Leu Asp Asp Leu Glu Leu Thr
305                 310                 315                 320

Leu Gly Ser Gly Thr Ala Arg Met
                325

<210> SEQ ID NO 3
<211> LENGTH: 984
<212> TYPE: DNA
<213> ORGANISM: Artificial Sequence
<220> FEATURE:
<223> OTHER INFORMATION: a gene obtained by mutating base C at position
      695 of SlBZR1L to T, which regulates the morphology of tomato
      fruits

<400> SEQUENCE: 3
atgatgtggg aaggtggagg gttgccggtg gagggtggtg gtggtgttgg tgaaggtggt       60
ggtgttggtg gtggtggagg tggtggtagt gggaggagga agccatcatg gagggaaagg      120
gagaataata ggaggaggga aggaggagga agggcaatag cagctaagat ttatagtgga      180
ttaagagcac aggggaatta taatcttcct aaacattgtg ataacaatga ggttttgaag      240
gctctttgtg ttgaagctgg atggattgtt gagcctgatg gaactactta tagaaaggga      300
tgcaggccaa ctccaatgga gattggaggc acttcagcca acattacgcc aagttcttca      360
cgaaatccaa gtcctccctc ttcatacttt gctagcccga ttccatctta ccaagttagt      420
ccaacatcct cgtctttccc aagtccatct cgtggtgatg ctaacatgtc gtcacatcca      480
tttgcatttc tccatagttc cattcccttg tcgctaccac cattacgaat atcaaacagt      540
gcccctgtaa caccacctct ttcatcacca actagagtcc ctaagcagat atttaatctt      600
gagactttgg ctagagagtc tatgtctgct ctaaatatcc ctttctttgc tgcttcagcc      660
ccaactagcc caactcgagg tcagcgattc actcttgcta caataccaga gtgtgacgaa      720
tctgattcat ccaccattga ttctggccag tggatgagct ttcaaaagta cgcagccaat      780
gggatcccta cttctccgac ttttaatctt attaagcctg tagctcagag aattccttct      840
aatgatatga tcatcgacaa gggtaagagc attgaatttg actttgagaa tgtatcagtt      900
aaggcagcat gggaaggtga aaagattcat gaggttggtt tagatgatct ggagctcact      960
ctcggaagtg ggactgctcg gatg                                             984

<210> SEQ ID NO 4
<211> LENGTH: 328
<212> TYPE: PRT
<213> ORGANISM: Artificial Sequence
<220> FEATURE:
<223> OTHER INFORMATION: amino acid sequence encoded by mSlBZR1L

<400> SEQUENCE: 4

-continued

| | | | | | | | | | | | | | | |
|---|---|---|---|---|---|---|---|---|---|---|---|---|---|---|
| Met<br>1 | Met | Trp | Glu | Gly<br>5 | Gly | Gly | Leu | Pro | Val<br>10 | Glu | Gly | Gly | Gly<br>15 | Val |
| Gly | Glu | Gly | Gly<br>20 | Gly | Val | Gly | Gly<br>25 | Gly | Gly | Gly | Gly<br>30 | Ser | Gly | Arg |
| Arg | Lys | Pro<br>35 | Ser | Trp | Arg | Glu<br>40 | Arg | Glu | Asn | Asn | Arg<br>45 | Arg | Arg | Glu | Arg |
| Arg | Arg<br>50 | Arg | Ala | Ile | Ala<br>55 | Ala | Lys | Ile | Tyr | Ser<br>60 | Gly | Leu | Arg | Ala | Gln |
| Gly<br>65 | Asn | Tyr | Asn | Leu | Pro<br>70 | Lys | His | Cys | Asp | Asn<br>75 | Asn | Glu | Val | Leu | Lys<br>80 |
| Ala | Leu | Cys | Val | Glu<br>85 | Ala | Gly | Trp | Ile | Val<br>90 | Glu | Pro | Asp | Gly | Thr<br>95 | Thr |
| Tyr | Arg | Lys | Gly<br>100 | Cys | Arg | Pro | Thr | Pro<br>105 | Met | Glu | Ile | Gly | Gly<br>110 | Thr | Ser |
| Ala | Asn | Ile<br>115 | Thr | Pro | Ser | Ser | Ser<br>120 | Arg | Asn | Pro | Ser | Pro<br>125 | Pro | Ser | Ser |
| Tyr | Phe<br>130 | Ala | Ser | Pro | Ile | Pro<br>135 | Ser | Tyr | Gln | Val | Ser<br>140 | Pro | Thr | Ser | Ser |
| Ser<br>145 | Phe | Pro | Ser | Pro | Ser<br>150 | Arg | Gly | Asp | Ala | Asn<br>155 | Met | Ser | Ser | His | Pro<br>160 |
| Phe | Ala | Phe | Leu | His<br>165 | Ser | Ser | Ile | Pro | Leu<br>170 | Ser | Leu | Pro | Pro | Leu<br>175 | Arg |
| Ile | Ser | Asn | Ser<br>180 | Ala | Pro | Val | Thr | Pro<br>185 | Pro | Leu | Ser | Ser | Pro<br>190 | Thr | Arg |
| Val | Pro | Lys<br>195 | Gln | Ile | Phe | Asn | Leu<br>200 | Glu | Thr | Leu | Ala | Arg<br>205 | Glu | Ser | Met |
| Ser | Ala<br>210 | Leu | Asn | Ile | Pro | Phe<br>215 | Phe | Ala | Ala | Ser | Ala<br>220 | Pro | Thr | Ser | Pro |
| Thr<br>225 | Arg | Gly | Gln | Arg | Phe<br>230 | Thr | Leu | Ala | Thr | Ile<br>235 | Pro | Glu | Cys | Asp | Glu<br>240 |
| Ser | Asp | Ser | Ser | Thr<br>245 | Ile | Asp | Ser | Gly | Gln<br>250 | Trp | Met | Ser | Phe | Gln<br>255 | Lys |
| Tyr | Ala | Ala | Asn<br>260 | Gly | Ile | Pro | Thr | Ser<br>265 | Pro | Thr | Phe | Asn | Leu<br>270 | Ile | Lys |
| Pro | Val | Ala<br>275 | Gln | Arg | Ile | Pro | Ser<br>280 | Asn | Asp | Met | Ile | Ile<br>285 | Asp | Lys | Gly |
| Lys | Ser<br>290 | Ile | Glu | Phe | Asp | Phe<br>295 | Glu | Asn | Val | Ser | Val<br>300 | Lys | Ala | Ala | Trp |
| Glu<br>305 | Gly | Glu | Lys | Ile | His<br>310 | Glu | Val | Gly | Leu | Asp<br>315 | Asp | Leu | Glu | Leu | Thr<br>320 |
| Leu | Gly | Ser | Gly | Thr<br>325 | Ala | Arg | Met | | | | | | | | |

What is claimed is:

1. A tomato mSlBZR1L gene comprising the nucleotide sequence of SEQ ID NO:3.

2. A nucleic acid construct comprising the gene of claim 1 operably linked to a promoter.

3. A tomato plant with altered fruit morphology comprising transgene comprising SEQ ID NO:3.

4. A method of altering fruit morphology in tomato comprising transforming a tomato plant with the nucleic acid construct of claim 2.

* * * * *